US011141292B1

United States Patent
Dubre

(10) Patent No.: US 11,141,292 B1
(45) Date of Patent: Oct. 12, 2021

(54) PROSTHETIC HAVING INTERCHANGEABLE INTERNAL CARTRIDGES

(71) Applicant: Darryl D Dubre, Nokomis, FL (US)

(72) Inventor: Darryl D Dubre, Nokomis, FL (US)

( * ) Notice: Subject to any disclaimer, the term of this patent is extended or adjusted under 35 U.S.C. 154(b) by 0 days.

(21) Appl. No.: 16/851,393

(22) Filed: Apr. 17, 2020

(51) Int. Cl.
*A61F 2/54* (2006.01)
*A61F 2/58* (2006.01)
*A61F 2/50* (2006.01)
*A61F 2/30* (2006.01)
*A61F 2/68* (2006.01)

(52) U.S. Cl.
CPC .... *A61F 2/588* (2013.01); *A61F 2002/30331* (2013.01); *A61F 2002/503* (2013.01); *A61F 2002/5072* (2013.01); *A61F 2002/5093* (2013.01); *A61F 2002/6854* (2013.01); *A61F 2220/0025* (2013.01)

(58) Field of Classification Search
CPC .... A61F 2/54; A61F 2/58; A61F 2/588; A61F 2002/5072; A61F 2002/6854; A61F 2002/586; A61F 2002/583
See application file for complete search history.

(56) References Cited

U.S. PATENT DOCUMENTS

| 2,364,313 | A | | 12/1944 | Pecorella | |
|---|---|---|---|---|---|
| 2,528,322 | A | * | 10/1950 | Syverud | A61F 2/583 |
| | | | | | 623/64 |
| 2,540,375 | A | | 2/1951 | Motis | |
| 2,545,542 | A | | 3/1951 | Fletcher | |
| 2,706,296 | A | | 4/1955 | fletcher et al. | |
| 3,413,658 | A | | 12/1968 | Becker | |
| 8,900,327 | B2 | | 12/2014 | Bertels et al. | |
| 9,474,631 | B2 | * | 10/2016 | Veatch | A61F 2/583 |
| 9,861,500 | B2 | * | 1/2018 | Puchhammer | A61F 2/588 |
| 2014/0081425 | A1 | * | 3/2014 | Sensinger | A61F 2/586 |
| | | | | | 623/64 |
| 2017/0209288 | A1 | * | 7/2017 | Veatch | A61F 2/588 |
| 2018/0338843 | A1 | * | 11/2018 | Kalmar | A61F 2/588 |

FOREIGN PATENT DOCUMENTS

FR 828272 2/1938

* cited by examiner

*Primary Examiner* — Bruce E Snow
(74) *Attorney, Agent, or Firm* — Henderson, Franklin, Starnes & Holt, P.A.; Luca L. Hickman

(57) ABSTRACT

A voluntary closing and locking prosthetic terminal device (1) having complex internal mechanisms configured into interchangeable cartridges (10) that provide end users with the capability of servicing the prosthetic on their own.

10 Claims, 2 Drawing Sheets

PROSTHETIC HAVING INTERCHANGEABLE INTERNAL CARTRIDGES

FIELD OF THE INVENTION

This invention relates to prosthetics and more particularly a voluntary closing and locking prosthetic hand/hook, also referred to as a terminal device, having complex internal mechanisms configured into interchangeable cartridges that provide end users with the capability of servicing the prosthetic on their own.

BACKGROUND OF THE INVENTION

A prosthetic hand/hook, also known as a terminal device, is an artificial device that replaces a missing body part and is intended to restore the normal functions of the missing body part. For example, a body powered split hook prosthetic terminal device replaces the grasping and holding functions of a missing hand. Body powered or cable operated hooks work by attaching a harness and cable around an opposite shoulder of the damaged arm. The user may then actuate the opening and/or closing of the split hook by moving his or her opposite shoulder.

Two types of body-powered prosthetic split hooks exist, voluntary opening "pull to open" and voluntary closing "pull to close." Virtually all "split hook" prostheses operate with a voluntary opening type system. Users of voluntary opening systems rely on simple designs that employ elastic bands for gripping force while users of voluntary closing systems rely on the user to apply tension for gripping force. A voluntary closing terminal device can be designed to lock closed allowing the user to hold an object without constant force input. The locking voluntary closing system is a superior prosthetic terminal device, but is not widely used due to a large upfront initial cost and more importantly the cost of maintenance. When a locking system on a user's voluntary closing device fails, the user normally must ship the prosthetic to a professional who can repair the internal parts. This is an expensive endeavor and leaves the user without his or her prosthetic for a period of days or weeks.

Therefore, a need exists for a prosthetic hook having complex internal mechanisms configured into interchangeable cartridges that provide end users with the capability of servicing the prosthetic on their own.

The relevant prior art includes the following references:

| U.S. Pat. No. (U.S. Patent References) | Inventor | Issue/Publication Date |
| --- | --- | --- |
| 2,706,296 | Fletcher et al. | Apr. 19, 1955 |
| 2,364,313 | Pecorella | Dec. 5, 1944 |
| 2,528,322 | Syverud et al. | Oct. 31, 1950 |
| 2,540,375 | Motis | Feb. 6, 1951 |
| 8,900,327 | Bertels et al. | Dec. 2, 2014 |
| 2,545,542 | Fletcher | Mar. 20, 1951 |
| 3,413,658 | Becker | Dec. 3, 1968 |
| FR828, 272 | Novelli | Feb. 7, 1938 |

SUMMARY OF THE INVENTION

The primary object of the present invention is to provide a prosthetic hook having complex internal mechanisms configured into interchangeable cartridges that provide end users with the capability of servicing the prosthetic terminal device on their own.

The present invention fulfills the above and other objects by providing a voluntary closing and locking system split hook prosthetic terminal device wherein the normally complex internal mechanisms have been replaced with interchangeable component cartridges that are easily interchangeable using one hand. The configuration of the interchangeable component cartridges allows for an added benefit of centering a cable support arm on the housing, thereby making the prosthetic terminal device capable of being used on a right arm or a left arm.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
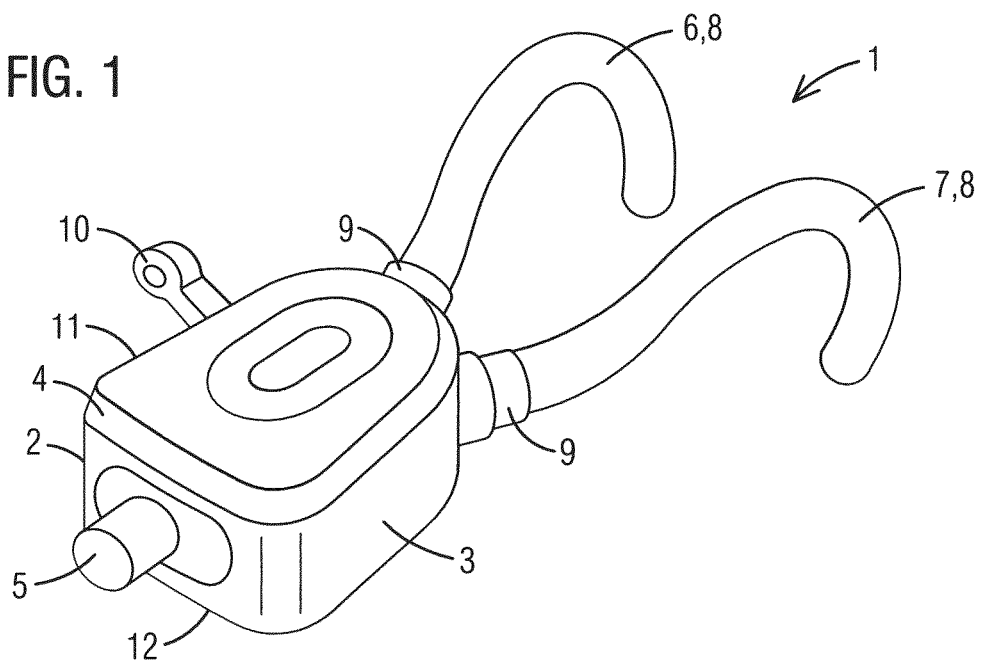
FIG. 1 is a top perspective view of a split hook prosthetic terminal device of the present invention.

For purposes of describing the preferred embodiment, the terminology used in reference to the numbered accessories in the drawings is as follows:

1. split hook prosthetic terminal device, generally
2. housing
3. base
4. cover
5. stud
6. first finger
7. second finger
8. split hook
9. keyed socket connection points
10. cable support arm member
11. top edge of housing
12. bottom edge of housing
13. circular-shaped recess
14. shaft
15. constant force spring
16. cable arm support member
17. second finger support member
18. engagement means
19. cartridge
20. first lever
21. second lever
22. locking mechanism
23. friction bar
24. friction pad
25. semi-circular locking cam
26. pin With reference to FIG. 1, a top view of a split hook prosthetic terminal device 1 of the present invention is illustrated. The split hook prosthetic terminal device 1 comprises a housing 2 having a base 3 and a cover 4. A stud 5 for mounting the split hook prosthetic terminal device 1 extends from a proximal end of the base 3, a first finger 6 and a second finger 7 that form the split hook 8 extend from a distal end of the base 3. The stud 5 is preferably molded into the base and/or integrated therein so the stud 5 and the base 3 form a single unit. The fingers 6 and 7 preferably have keyed socket connection points 9 with the housing 2 and second finger support member 17 to allow the fingers 6, 7 to be rotated.

A cable support arm 10 extends from the cable arm support member 16 and is centered between a top edge 11 of the cover 4 and a bottom edge 12 of the base 3. The centered position of the cable support arm 10 allows the split hook prosthetic terminal device 1 to be ambidextrous and worn on the right or left arm. This is in contrast to a conventional voluntary closing split hook design, which have off set cable support arms, thereby limiting each device to a right-handed device or a left-handed device.

Figure 2:
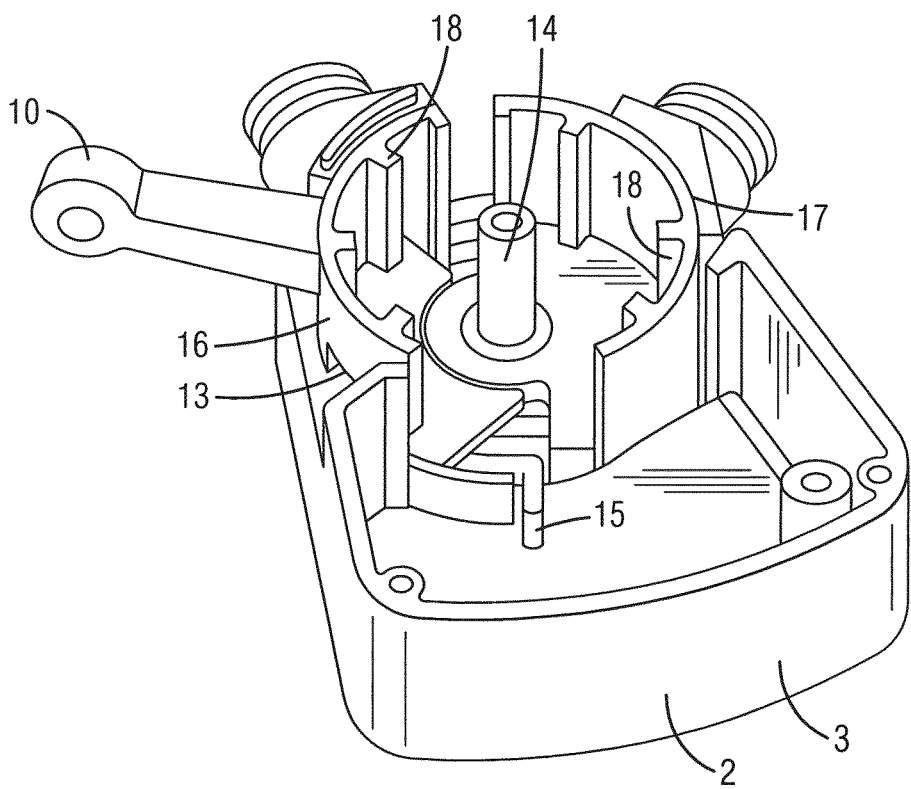
FIG. 2 is a top perspective view of an open housing of the split hook prosthetic terminal device of the present invention wherein the cartridge has been removed from the housing.

With reference to FIG. 2, a top perspective view of an open housing 2 of the split hook prosthetic terminal device 1 of the present invention wherein a cartridge 19 has been removed from the housing 2 is illustrated.

An internal portion of the base 3 of the housing 2 forms a circular-shaped recess 13 having a shaft 14 centered therein. The shaft 14 supports a constant force spring 15, such as a flat spiral spring or torsion spring. A cable arm support member 16 is supported by the shaft 14 within the circular-shaped recess 13 above the constant force spring 15. The cable arm support member 16 supports cable support arm 10 as illustrated in FIG. 1. The cable arm support member 16 and a second finger support member 17 are the support carrier for the cartridge 19. The second finger support member 17 supports the second finger 7 which is capable of being actuated by engaging the cable support arm 10 when the cartridge 19 is inserted, as illustrated in FIG. 1.

The cable arm support member 16 and the second finger support member 17 are each rotational around the shaft 14, thereby allowing each to rotate and actuate the second finger 7 when the cable support arm 10 is actuated.

One or more engagement means 18, such as a mirrored profile, channels, slots, ridges, tabs and so forth are located on an interior surface of the cable arm support member 16 and the second finger support member 17.

Figure 3:
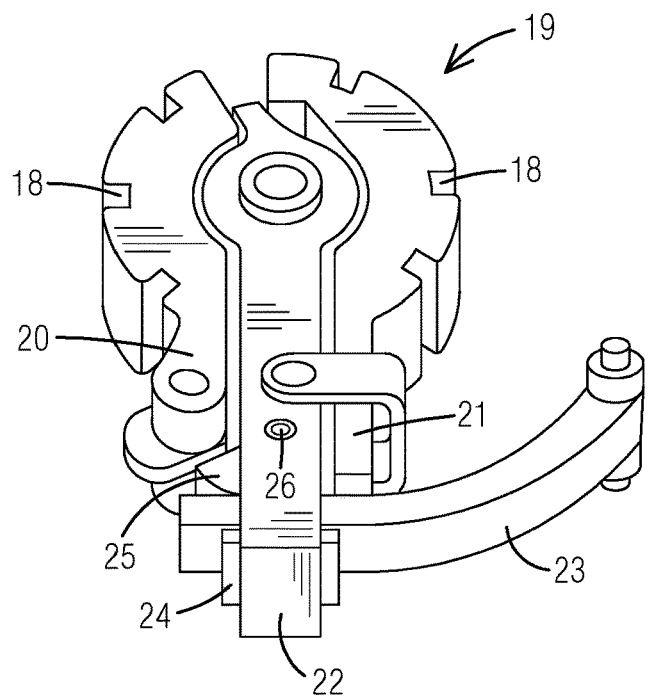
FIG. 3 is a top perspective view of a cartridge of a split hook prosthetic terminal device of the present invention.

With reference to FIG. 3, a top perspective view of a cartridge 19 of a split hook prosthetic terminal device 1 of the present invention is illustrated. The cartridge 19 comprises a first lever 20 and second lever 21, each attached to a U-shaped locking mechanism 22 that is slidably attached to a curved friction bar 23. The U-shaped locking mechanism 22 consists of a friction pad 24 and a semi-circular locking cam 25. The semi-circular locking cam 25 pivots on pin 26, and engages curved friction bar to actuate locking the device in a closed position. The components of the cartridge 19 assist in maintaining the split hook 8 in a locked and grasping position after the cable support arm 10 has been actuated to close the split hook 8.

One or more engagement means 18, such as a mirrored profile, channels, slots, ridges, tabs and so forth, are located on an exterior surface of the first lever 20 and second lever 21 to engage the cable arm support member 16 and the second finger support member 17.

Figure 4:
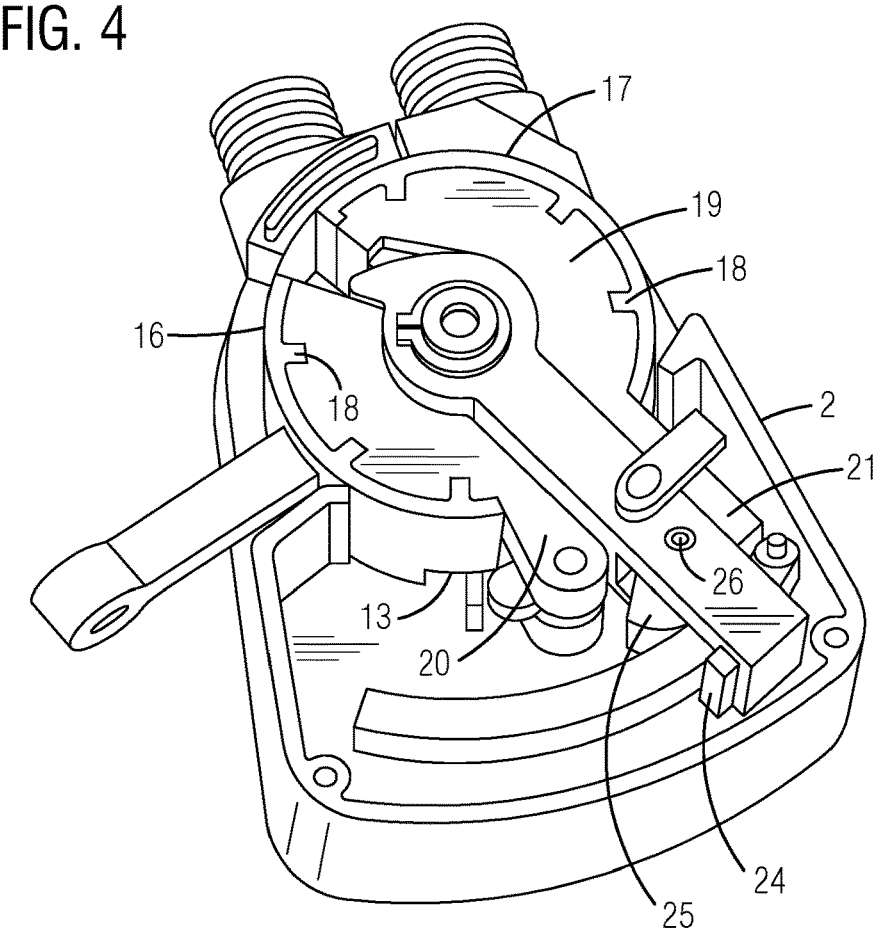
FIG. 4 is a top perspective view of a cartridge inserted into a housing of a split hook prosthetic terminal device of the present invention.

With reference to FIG. 4, a top perspective view of a cartridge 19 inserted into the cable arm support member 16 and second finger support member 17 of a split hook prosthetic terminal device 1 of the present invention is illustrated. One or more engagement means 18, such as a mirrored profile, channels, slots, ridges, tabs and so forth are located on an exterior surface of the first lever 20 and an exterior surface of the second lever 21 to engage one or more engagement means 18 located on interior surfaces of the cable arm support member 16 and the second finger support member 17. The cartridge 19 and components thereof work to maintain said cable arm support member 16 and said second finger support member 17 in temporarily locked positions to grasp objects.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A split hook prosthetic terminal device comprising:
    a housing having a base and a cover;
    a stud for mounting the split hook prosthetic terminal device extending from a proximal end of said housing;
    a first finger and a second finger extending from a distal end of said housing and forming a split hook;
    a cable support arm extending from said housing;
    an internal portion of said housing forming a circular-shaped recess having a shaft centered therein;
    said shaft and circular-shaped recess supporting a constant force spring below a cable arm support member and a second finger support member;
    a cartridge that is insertable into said cable arm support member and second finger support member; and
    said cartridge having at least two components that work to maintain said cable arm support member and said second finger support member in temporarily locked positions.

2. The split hook prosthetic terminal device of claim 1 further wherein:
    said cartridge comprises a first lever and second lever each attached to a U-shaped mechanism that is slidably attached to a curved friction bar.

3. The split hook prosthetic terminal device of claim 1 further comprising:
    at least one engagement means located on an interior surface of the first finger support member;
    at least one engagement means located on an interior surface of the second finger support member, and
    at least one engagement means located on an exterior surface of the cartridge that engages the cable arm support member and the second finger support member.

4. The split hook prosthetic terminal device of claim 2 further comprising:
    at least one engagement means located on an interior surface of the cable arm support member;
    at least one engagement means located on an interior surface of the second finger support member; and
    at least one engagement means located on an exterior surface of the cartridge that engages the cable arm support member and the second finger support member.

5. The split hook prosthetic terminal device of claim 1 further wherein:
    said cable arm support member is centered between a top edge of the cover and a bottom edge of the base.

6. A split hook prosthetic terminal device comprising:
    a housing having a base and a cover;
    a stud for mounting the split hook prosthetic terminal device extending from a proximal end of said housing;

a first finger and a second finger extending from a distal end of said housing and forming a split hook;

a cable support arm extending from said housing;

an internal portion of said housing forming a circular-shaped recess having a shaft centered therein;

said shaft and circular-shaped recess supporting a constant force spring below a cable arm support member and a second finger support member;

a cartridge that is insertable into said circular-shaped recess;

said cartridge having at least two components that work to maintain said cable arm support member and said second finger support member in temporarily locked positions; and said cartridge comprises a first lever and second lever each attached to a U-shaped locking mechanism that is slidably attached to a curved friction bar.

7. The split hook prosthetic terminal device of claim 6 further comprising:

at least one engagement means located on an interior surface of the cable arm support member;

at least one engagement means located on an interior surface of the second finger support member; and at least one engagement means located on an exterior surface of the cartridge that engages the cable arm support member and the second finger support member.

8. The split hook prosthetic terminal device of claim 6 further wherein:

said cable arm support member is centered between a top edge of the cover and a bottom edge of the base.

9. A split hook prosthetic terminal device comprising:

a housing having a base and a cover;

a stud for mounting the split hook prosthetic terminal device extending from a proximal end of said housing;

a first finger and a second finger extending from a distal end of said housing and forming a split hook;

a cable support arm member extending from said housing;

an internal portion of said housing forming a circular-shaped recess having a shaft centered therein;

said shaft and circular-shaped recess supporting a constant force spring below a cable arm support member and a second finger support member;

a cartridge that is insertable into said circular-shaped recess;

said cartridge having at least two components that work to maintain said cable arm support member and said second finger support member in temporarily locked positions;

said cartridge comprises a first lever and second lever each attached to a U-shaped locking mechanism that is slidably attached to a curved friction bar;

at least one engagement means located on an interior surface of the cable arm support member;

at least one engagement means located on an interior surface of the second finger support member; and at least one engagement means located on an exterior surface of the cartridge that engages the cable arm support member and the second finger support member.

10. The split hook prosthetic terminal device of claim 9 further wherein:

said cable arm support member is centered between a top edge of the cover and a bottom edge of the base.

\* \* \* \* \*